(12) United States Patent
Datzmann et al.

(10) Patent No.: US 6,379,593 B1
(45) Date of Patent: *Apr. 30, 2002

(54) METHOD FOR MANUFACTURING A MULTI-COLORED SHAPED BODY FOR FURTHER PROCESSING TO OBTAIN A DENTAL RESTORATION

(75) Inventors: Gabriele Datzmann, Dresden; Regina Kuhnert, Radeberg; Michael Neumann, Berlin, all of (DE)

(73) Assignee: Mega-Physik GmbH Co. KG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/055,828

(22) Filed: Apr. 6, 1998

(30) Foreign Application Priority Data

Apr. 7, 1997 (DE) .......................................... 197 14 178

(51) Int. Cl.[7] .............................................. A61C 13/00
(52) U.S. Cl. .............................. 264/20; 264/16; 264/19; 433/167; 433/203.1
(58) Field of Search ................................ 264/16, 19, 20

(56) References Cited

U.S. PATENT DOCUMENTS

| 1,599,084 | A | * | 9/1926 | Gibson | ......................... 264/20 |
| 2,314,957 | A | * | 3/1943 | Thornton et al. | ............. 264/20 |
| 2,677,150 | A | * | 5/1954 | Rydin | ........................... 264/20 |
| 3,181,240 | A | * | 5/1965 | Kerhart et al. | ................ 264/20 |
| 5,217,375 | A | * | 6/1993 | Oden | ......................... 433/218 |
| 5,575,653 | A | * | 11/1996 | Freyer et al. | ................. 264/20 |
| 5,653,791 | A | * | 8/1997 | Panzera et al. | |

FOREIGN PATENT DOCUMENTS

| DE | 760 351 | 5/1951 |
| DE | 758 675 | 5/1953 |
| DE | 27 49 564 C2 | 5/1979 |
| DE | 235 557 A1 | 5/1986 |
| EP | 0 332 887 | 9/1989 |
| EP | 0 599 187 A1 | 6/1994 |

* cited by examiner

*Primary Examiner*—James Derrington
(74) *Attorney, Agent, or Firm*—Pendorf & Cutliff

(57) ABSTRACT

The present invention relates to a method for producing a multicolored shaped body for further processing to form a dental restoration, and to a device for carrying out the method.

19 Claims, No Drawings

METHOD FOR MANUFACTURING A MULTI-COLORED SHAPED BODY FOR FURTHER PROCESSING TO OBTAIN A DENTAL RESTORATION

BACKGROUND OF THE INVENTION

1. Field of the Invention

The present invention relates to a method for producing a multi-colored shaped body for further processing to form a dental restoration, and to an article produced thereby.

2. Description of the Related Art

The background to the invention is the sector of dental engineering, where the dental restoration, for example a dental crown, an inlay, an onlay or a veneer, is produced from a ceramic shaped body or a plastic shaped body. This production is increasingly carried out using machines, suitable processes being the CAD/CAM process or the copy-milling process.

In order to satisfy aesthetic requirements and to achieve dental restorations whose coloring does not differ, or scarcely differs, from the color, or even discolorations, of natural teeth, multicolored shaped bodies are produced.

EP 0 455 854 A1 discloses, for example, a ceramic shaped article made from customary ceramic or porcelain material having a plurality of differently colored layers ranging from vitreously translucent in the occlusal region to yellowish opaque in the cervical region. However, this document does not reveal any details as to how the multilayered, multicolored shaped article is produced.

Furthermore, U.S. Pat. No. 4,970,032 discloses a multi-colored plastic shaped article having predetermined, varying colored layers, which are arranged above one another around a core. An injection-molding process is used to produce the core and the layers. The result is a block whose colored layers are clearly demarcated from one another, a fact which is incompatible with any approximation of the natural color of a tooth.

Based on this prior art, the object of the invention is to provide a method for producing a multicolored shaped body for further processing to form a dental restoration, which method can be used both for ceramic shaped bodies and for plastic shaped bodies, is cost-effective and allows a continuous color transition.

SUMMARY OF THE INVENTION

With regard to the method, the abovementioned object is achieved by means of the features of the present invention, in accordance with which at least two starting materials of different colors are introduced into a compacting die, which essentially predetermines the shape of the shaped body, and are pressed to form the shaped body.

According to the invention, it is recognized that the color transition can be set in an optimum manner, in accordance with the high demands placed on the aesthetics of the color of the tooth, irrespective of the starting material if the starting materials are pressed together. The contact surfaces are subjected to pressure, and the differently colored starting materials are brought into intimate contact in the interface region, so that mingling—even if only slight—takes place in that area. This mingling, which can be affected by the shape and size of the particles of the starting materials and/or by the pressure applied, enables a flowing color transition to be achieved and means that the actual interface between the starting materials is not visible. On the other hand, the pressing process may optionally also be used to produce color regions which are clearly delimited from one another. The use of the pressing process allows both plastic and ceramic to be used as starting materials at low costs, owing to reduced preparation expenditure.

DETAILED DESCRIPTION OF THE INVENTION

According to a preferred exemplary embodiment, the starting materials are introduced successively preferably in the form of layers into the compacting die. A plurality of layers may be formed which have different or identical layer thicknesses. The layers thus formed may be horizontal and/or vertical. Especially for forming vertical layers, a separating partition may be provided in the die which is removed prior to pressing. As an alternative, filling could also take place in such a manner that a plurality of starting materials are introduced simultaneously at different points in the die, enabling a vertical layered profile to be achieved. The starting materials could also, for example, be introduced in the form of rings, which is advantageous, for example, for crowns, in which the position of the color components is particularly important.

The shaped body is particularly preferably produced by dry-pressing, during which the particles of the starting materials at the interfaces blend into one another and form the mixed layer in a particularly intimate manner. In a known way, pressing auxiliaries such as lubricants or binders could be added to the starting materials for dry-pressing purposes. For ceramic starting materials, polyvinyl alcohols, cellulose derivatives and alginates could be used as binders and wax could be used as a lubricant.

According to a further exemplary embodiment, the starting materials could be subjected to the action of heat during the dry-pressing operation. This also affects properties other than the color, in particular the strength of the shaped body, on the one hand in the starting materials, and on the other hand in the region of the starting materials adjoining one another. In the case of ceramic starting materials, hot isostatic pressing is suitable, while in the case of plastics hot press molding using heated dies is suitable.

The shaped body which has been pressed and removed from the die could also be subjected to a heat treatment, in particular in order to increase its strength. A subsequent heat treatment can also be used to set other microstructural properties.

The advantageous possibility which has already been explained above of using the pressing process to produce starting materials or layers which merge continuously into one another could be manipulated as desired by using more or less contrasting colors.

In order to ensure satisfactory compatibility between the starting materials, the latter could have essentially the same chemical composition and differ only with regard to their color. In terms of the physical condition of the starting materials, they may be present as powders, granules or plastic masses. Here too, it is advantageous if all the starting materials for a shaped body are placed in the same compactable mold.

As already mentioned above, a ceramic material could be used as the starting material. Consideration could be given to a ceramic material which is based on natural feldspar or oxide ceramics. However, it is preferred to use a ceramic material which is produced synthetically and is based on metal oxides, namely at least $SiO_2$, $K_2O$ and $Al_2O_3$ and/or the nitrates and carbonates thereof. The ceramic material could also consist of mixtures of oxide ceramics and/or natural feldspar and the synthetic material or a mixture of natural feldspar and one or more metal oxides.

The synthetic ceramic is very advantageous by comparison with ceramic shaped bodies made of natural feldspar ceramic. In the case of natural feldspar ceramic, natural raw materials are employed, a fact which entails a number of drawbacks. Only very pure feldspars can be used in order to satisfy the visual demands placed on dental restorations. Such pure raw materials are difficult and expensive to procure. Even very pure feldspars have to be sorted manually, since it is necessary to screen out naturally occurring impurities. Moreover, natural feldspars exhibit different melting behaviors depending on their geological history, making the production method difficult to reproduce—for example with regard to firing temperatures and firing times—and impairing the quality.

With regard to the use of synthetic ceramic, it has been recognized as advantageous that it is possible to achieve cost-effective production, a quality level which is essentially free of fluctuation, and hence also good reproducibility of a shaped body if the latter consists of a synthetic material and if pure metal oxides or the nitrates or carbonates thereof or metal oxide compounds are used as starting materials in the method. This precludes natural impurities or procurement problems found with natural raw materials. Moreover, the cost benefits also result from the fact that the pure metal oxides or metal oxide compounds can be produced on an industrial scale, from their constant product quality, from shorter manufacturing times during processing and from a higher transparency owing to their purity.

The preferred synthetic ceramic material, which—in a similar manner to a modular system—can be modified using further substances in order to achieve specific properties, has the following basic batch composition:

| | |
|---|---|
| $SiO_2$ | 58 to 65% |
| $Al_2O_3$ | 10 to 16% |
| $K_2O$ | 12 to 18% |
| $NA_2O$ | 1 to 5% |
| CaO | 1 to 5% |
| $Li_2O$ | 0 to 5% |
| $B_2O_3$ | 0 to 5% |

The synthetic ceramic material is obtained by mixing the metal oxides, the carbonates and/or nitrates thereof, preferably in the dry state, by melting or sintering the mixture, preferably at temperatures of from 1350° C. to 1600° C., to obtain a leucite-containing frit, and by tempering the frit obtained in this way at temperatures of from 600° C. to 1000° C. and then bringing it into a form in which it can be pressed.

During the melting or sintering of the metal oxide mixture, two phases—namely the leucite crystals, on the one hand, and the glass phase, on the other hand—are formed. A controlled tempering operation, with holding times in various temperature ranges of from approximately 1 h to 10 h could follow, in order to achieve the desired quality and quantity of the leucite crystals. In order for it to be possible for the frit to be processed further to form the shaped body, it is converted into a form which is suitable for the pressing process. Firstly, the tempered frit, which is present in the form of large pieces, it comminuted to a particle size of approximately 10 μm. The powder obtained in this way could now be pressed directly to form the shaped body. However, with a view to better processability, it is preferred to disperse the powder, to pump it into a spray dryer or fluidized-bed dryer, and to obtain granules which are pressed to form the shaped body.

Before shaping the article, the frit could be modified using further materials, so that properties of the starting material can be adjusted in a controlled manner. The frit is preferably modified after comminution has taken place. The further material could be mixed in the dry state with the frit powder, for example in a mill, or could also be dispersed to form a slip. The preparation of a slip is preferred if it is in any case intended to provide granules for pressing.

By modifying the frit, it would be possible, for example, to change the coefficient of thermal expansion, the firing temperature, the transparency or the strength. To alter the abovementioned properties in a controlled manner, the frit could be blended with a further frit.

To increase the strength and/or the coefficient of thermal expansion, two frits, having the following basic batch compositions, have proven suitable:

| (1) | |
|---|---|
| $SiO_2$ | 50 to 55% |
| $Al_2O_3$ | 18 to 25% |
| $K_2O$ | 13 to 20% |
| $NA_2O$ | 1 to 5% |
| CaO | 0 to 3% |
| $Li_2O$ | 0 to 5% |
| $TiO_2$ | 2 to 8% |

| (2) | |
|---|---|
| $SiO_2$ | 50 to 55% |
| $Al_2O_3$ | 18 to 25% |
| $K_2O$ | 13 to 20% |
| $NA_2O$ | 1 to 5% |
| CaO | 0 to 3% |
| $Li_2O$ | 0 to 5% |
| $TiO_2$ | 0 to 3% |
| $B_2O_3$ | 0 to 3% |

Increasing the strength plays an important role with regard to the mastication stresses of the dental restoration. Moreover, the high strength is also relevant to the further processing of the shaped body to form the dental restoration. During further processing, various machine tools, such as milling and grinding tools, which subject the shaped article to substantial forces, are used.

To improve the transparency, a frit having the following basic batch composition has proven advantageous:

| | |
|---|---|
| $SiO_2$ | 60 to 65% |
| $Al_2O_3$ | 10 to 15% |
| $K_2O$ | 10 to 15% |
| $NA_2O$ | 2 to 7% |
| CaO | 1 to 5% |
| $Li_2O$ | 0 to 1% |
| $TiO_2$ | 0 to 3% |
| $B_2O_3$ | 0 to 3% |

It would also be possible to affect the luminescence of the frit, which is important in particular with regard to the use of the dental restoration and the associated aesthetic requirements. In particular, a fluorescence agent could be added to the frit in order to adjust the fluorescence.

A further modification to the frit, which modification is significant to the teaching of the invention with regard to the multicolored nature of the shaped articles, is the possibility of adjusting its color. In the dental engineering field, it is necessary to provide very different tooth colors, in order to be able to match the individual tooth colors of the patients. Various pigments could be added to the frit, so that a range of frits of different colors can be provided and so that it is possible to achieve extremely fine color shade charts, to match the colors which are found on the individual natural tooth.

According to a further exemplary embodiment, a layer of a heat-treated, multicolored shaped article could have the following basic batch composition:

| | |
|---|---|
| $SiO_2$ | 58 to 65% |
| $Al_2O_3$ | 13 to 20% |
| $K_2O$ | 11 to 18% |
| $NA_2O$ | 1 to 6% |
| CaO | 0 to 4% |
| $Li_2O$ | 0 to 1% |
| $TiO_2$ | 0 to 2% |
| $B_2O_3$ | 0 to 4% |

At this point it is expressly pointed out that the basic batch compositions and the modified basic batch compositions of the synthetic ceramic material can most certainly also be used to produce ceramic shaped articles of a single color.

The shaped article obtained by the pressure shaping could now be sintered at temperatures of from 700° C. to 1200° C., specifically in vacuo. Sintering in vacuo has a positive effect on the transparency, since gas inclusions are avoided. It has proven particularly advantageous to carry out subsequent tempering of the shaped article, thus adjusting the proportion of leucite and the size of the leucite crystals. In order to achieve a uniform temperature distribution on and in the shaped article, a shaped article having horizontal color stratification is fired in a vertical position, so that all the colored layers at the end side of the shaped article are in contact with the firing substrate.

The heat treated shaped body has a strength greater than 100 MPa, perferably a strength of from 100 MPa to 300 MPa and more preferably of 100 MPa to 180 MPa.

It should be emphasized that production is cost-effective, since a synthetic glass ceramic is used which is based on starting materials which are obtained synthetically and therefore can be produced on an industrial scale and cost-effectively. Moreover, a shaped body of this kind has a high transparency and exhibits a so-called chameleon effect, which allows it to be adapted well to the natural tooth color. Moreover, the two-phase structure of the glass ceramic, namely leucite and glass, assists, owing to its very good etchability, with adhesive attachment to the tooth which is of good quality and is operationally secure.

As an alternative to a ceramic starting material, a plastic could also be used as starting material. It is preferred to use a polymerizable plastic based on acrylate/methacrylate and/or polacrylate/polymethacrylate or urethanes/polyurethanes, or mixtures thereof. To adjust the color, pigments could be added to the plastic, and/or fluorescence agents could be added to the plastic in order to adjust the fluorescence. A press-molded plastic shaped body could likewise be subjected to a heat treatment, in order to strengthen the plastic. The strengthening is effected via a polymerization reaction. As an alternative, or in addition, in order to provide strength, the press-molded plastic shaped body could be irradiated with high-energy gamma radiation and/or ultraviolet radiation and/or visible radiation and/or thermal radiation.

It is particularly advantageous, with regard to the further processing by machine of the ceramic shaped body to form a dental restoration, namely inlays, onlays, veneers or crowns, if the shaped body can be assembled with a retaining device. The holding device could then be integrated in a known manner in a machine tool. It is also conceivable to clamp the shaped body directly into a machine tool, without a retaining device.

For performing the inventive method the invention provides a device, wherein separate auxiliary devices, such as slides, chutes, feedpipes, vibrating chutes and filling shoes, can be assigned to a press, in particular a dry press, for separately filling the die of the pressing tool with the starting materials of different colors.

Filling shoes have proven successful for successively filling the die of the pressing tool with the starting materials of different colors. Depending on which colored layer is to be produced and on the height to which it is to be filled, the respective filling shoe is attached to the dry-pressing machine and emptied into the die. It is particularly advantageous if one filling shoe is provided for each color hue of the starting materials of different colors. This prevents contaminations and associated color discrepancies.

The pressing tool can be used to achieve a very wide variety of shapes of the shaped body. According to one exemplary embodiment, the pressing tool could be configured in such a manner that a depression is formed when the shaped body is pressed. The depression is advantageous with regard to the internal machining of a dental crown. According to a further embodiment, the ceramic shaped body could be provided with a depression for the internal machining of a dental crown even during the shaping process. To do this, it is necessary for the pressing tool to have a suitable form for producing the depression.

For distributing the starting materials, a removable partition may be provided, which is inserted into the die and removed directly before pressing. In addition, the form of the pressing ram could exert a shaping action on the starting materials which have been placed in the die.

Finally, it is pointed out that the teaching according to the invention is not limited to the exemplary embodiments explained above. Rather, a very wide variety of ceramic batch compositions or plastic mixtures, or other materials which have not yet been considered here are possible starting materials.

Now that the invention has been described,

What is claimed is:

1. A method for producing a multi-colored shaped body suitable for further processing to form a dental restoration by a CAD/CAM or a copy milling process, said method comprising:
   (a) obtaining at least first and second ceramic materials, each of which have been subjected to tempering to produce a homogeneous mass comprising glass and crystal phases, wherein said first and second ceramic materials differ in color after sintering;
   (b) introducing an amount of said first ceramic material into a compacting die;
   (c) introducing an amount of said second ceramic material into said compacting die;
   (d) applying pressure to said ceramic materials in said compacting dye; and
   (e) sintering the product of step (d) at a temperature from 700 to 1200° C., to form a multi-colored shaped body wherein said first ceramic material and said second ceramic material are materials of different colors.

2. The method as claimed in claim 1, wherein the ceramic materials introduced into the compacting die are in the form of granules.

3. The method as claimed in claim 2, wherein a pigment and/or a fluorescence agent is added to a base material prior to granulation, in order to produce the granular ceramic material.

4. The method according to claim 1, wherein the ceramic material is based on natural feldspar or a mixture of natural feldspar and metal oxides.

5. The method as claimed in claim 4, wherein the ceramic material is at least in part a synthetic material, which is based at least on $SiO_2$, $K_2O$ and $Al_2O_2$.

6. The method as claimed in claim 5, wherein the synthetic ceramic material has the following basic batch composition:

| | |
|---|---|
| $SiO_2$ | 58 to 65% |
| $Al_2O_3$ | 10 to 16% |
| $K_2O$ | 12 to 18% |
| $Na_2O$ | 1 to 5% |
| CaO | 1 to 5% |
| $Li_2O$ | 0 to 5% |
| $B_2O_3$ | 0 to 5% |

7. The method as claimed in claim 5, wherein the synthetic ceramic material is obtained by mixing the metal oxides, the carbonates and/or nitrates thereof, by melting or sintering the mixture at temperatures of from 1350° C. to 1600° C. to obtain a leucite-containing frit, and by tempering the frit obtained in this way at temperatures of from 600° C. to 1000° C. and then bringing it into a form in which it can be pressed.

8. The method as claimed in claim 7, wherein the frit, in order to increase the strength and/or the coefficient of thermal expansion, is blended with a further frit, which has the following basic batch composition:

| | |
|---|---|
| $SiO_2$ | 50 to 55% |
| $Al_2O_3$ | 18 to 25% |
| $K_2O$ | 13 to 20% |
| $Na_2O$ | 1 to 5% |
| CaO | 0 to 3% |
| $Li_2O$ | 0 to 5% |
| $TiO_2$ | 2 to 8% |

9. The method as claimed in claim 7, wherein the frit, in order to increase the strength and/or the coefficient of thermal expansion, is blended with a further frit, which has the following basic batch composition:

| | |
|---|---|
| $SiO_2$ | 50 to 55% |
| $Al_2O_3$ | 18 to 25% |
| $K_2O$ | 13 to 20% |
| $Na_2O$ | 1 to 5% |
| CaO | 0 to 3% |
| $Li_2O$ | 0 to 5% |

| | |
|---|---|
| -continued | |
| $TiO_2$ | 0 to 3% |
| $B_2O_3$ | 0 to 3% |

10. The method as claimed in claim 7, wherein the frit, in order to increase the transparency, is blended with a further frit, which has the following basic batch composition:

| | |
|---|---|
| $SiO_2$ | 60 to 65% |
| $Al_2O_3$ | 10 to 15% |
| $K_2O$ | 10 to 15% |
| $Na_2O$ | 2 to 7% |
| CaO | 1 to 5% |
| $Li_2O$ | 0 to 1% |
| $TiO_2$ | 0 to 3% |
| $B_2O_3$ | 0 to 3% |

11. The method as claimed in claim 5, wherein the synthetic ceramic material of a shaped body has the following basic batch composition:

| | |
|---|---|
| $SiO_2$ | 58 to 65% |
| $Al_2O_3$ | 13 to 20% |
| $K_2O$ | 11 to 18% |
| $Na_2O$ | 1 to 6% |
| CaO | 0 to 4% |
| $Li_2O$ | 0 to 1% |
| $TiO_2$ | 0 to 2% |
| $B_2O_3$ | 0 to 4% |

12. The method as claimed in claim 1, wherein the shaped body is subjected to a tempering operation.

13. The method as claimed in claim 1, wherein the ceramic materials are introduced into the compacting die in the form of layers.

14. The method as claimed in claim 1, comprising the step of dry-pressing of the ceramic materials.

15. The method as claimed in claim 14, wherein the ceramic materials are subjected to the action of heat during the dry-pressing operation.

16. A method as in claim 1, further comprising assembling said article with a retaining device and then processing further by machine to form a dental restoration.

17. The method as in claim 1, wherein mixing of the ceramic materials is carried out in the dry state.

18. The method as claimed in claim 1, wherein the shaped-article blank is sintered in vacuo.

19. The method as claimed in claim 1, wherein said tempering is accomplished at temperature of from 600° C. to 1000° C.

* * * * *

UNITED STATES PATENT AND TRADEMARK OFFICE
CERTIFICATE OF CORRECTION

PATENT NO.    : 6,379,593 B1                                         Page 1 of 1
DATED         : April 30, 2002
INVENTOR(S)   : Gabriele Datzmann, Regina Kuhnert and Michael Neumann It is certified that error appears in the above-identified patent and that said Letters Patent is hereby corrected as shown below:

<u>Title page,</u>
Item [73], Assignee, should read:
-- [73]  Assignee: Ivoclar Vivadent AG (LI) --

Signed and Sealed this

Twenty-eighth Day of October, 2003

JAMES E. ROGAN
*Director of the United States Patent and Trademark Office*